United States Patent
Reitmeier et al.

(10) Patent No.: US 9,939,397 B2
(45) Date of Patent: Apr. 10, 2018

(54) SENSOR FOR DETECTING OXIDIZABLE GASES

(71) Applicant: Continental Automotive GmbH, Hannover (DE)

(72) Inventors: Willibald Reitmeier, Hohenschambach (DE); Ralf Moos, Bayreuth (DE); Gunter Hagen, Schwarzenbach a. Wald (DE); Daniela Schoenauer-Kamin, Heinersreuth (DE); Joroslaw Kita, Bayreuth (DE); Sven Wiegaertner, Pottenstein (DE)

(73) Assignee: CONTINENTAL AUTOMOTIVE GMBH, Hanover (DE)

( * ) Notice: Subject to any disclaimer, the term of this patent is extended or adjusted under 35 U.S.C. 154(b) by 255 days.

(21) Appl. No.: 14/915,951

(22) PCT Filed: Sep. 1, 2014

(86) PCT No.: PCT/EP2014/068495
§ 371 (c)(1),
(2) Date: Mar. 2, 2016

(87) PCT Pub. No.: WO2015/028660
PCT Pub. Date: Mar. 5, 2015

(65) Prior Publication Data
US 2016/0195483 A1 Jul. 7, 2016

(30) Foreign Application Priority Data
Sep. 2, 2013 (DE) .................. 10 2013 217 465

(51) Int. Cl.
*G01N 25/32* (2006.01)
*G01N 33/22* (2006.01)
*G01N 33/00* (2006.01)

(52) U.S. Cl.
CPC ........... *G01N 25/32* (2013.01); *G01N 33/004* (2013.01); *G01N 33/005* (2013.01); *G01N 33/0047* (2013.01)

(58) Field of Classification Search
CPC ............................... G01N 25/32; G01N 33/22
(Continued)

(56) References Cited

U.S. PATENT DOCUMENTS

| 4,063,898 A | 12/1977 | Fisher .............................. 422/94 |
| 4,343,768 A * | 8/1982 | Kimura .................. G01N 27/16 338/34 |

(Continued)

FOREIGN PATENT DOCUMENTS

| DE | 3932880 A1 | 4/1991 | ............. G01N 27/16 |
| DE | 4317568 C2 | 9/1997 | ............. G01N 25/32 |

(Continued)

OTHER PUBLICATIONS

German Office Action, Application No. 102013217465.9, 5 pages, dated Apr. 14, 2014.
(Continued)

*Primary Examiner* — Arlen Soderquist
(74) *Attorney, Agent, or Firm* — Slayden Grubert Beard PLLC

(57) ABSTRACT

A sensor for detecting oxidizable gases may comprise a catalytically inactive surface and a catalytically active surface on opposite sides of a sensor element and a thermal element running through the sensor element to connect the two surfaces, with a device for measuring a thermoelectric voltage between the catalytically active surface and the inactive surface as a measure of the difference in temperature and therefore the gas concentration. The sensor may include a hot plate mounted on a base carrier by means of narrow arms, wherein the thermal element includes at least (Continued)

one via extending through the hot plate and connecting the two surfaces to one another, and in the region of which the thermoelectric voltage is measured.

19 Claims, 2 Drawing Sheets

(58) Field of Classification Search
USPC ........ 422/90, 94–95, 98; 436/134, 141, 144, 436/151–152, 159
See application file for complete search history.

(56) References Cited

U.S. PATENT DOCUMENTS

| | | | | |
|---|---|---|---|---|
| 4,359,709 A | * | 11/1982 | Nakatani | G01N 27/12 338/34 |
| 4,421,720 A | * | 12/1983 | Kamiya | G01N 27/16 422/97 |
| 4,835,108 A | | 5/1989 | Cooper | 436/137 |
| 5,356,756 A | * | 10/1994 | Cavicchi | G01N 27/18 204/192.12 |
| 5,451,371 A | * | 9/1995 | Zanini-Fisher | G01N 27/16 204/424 |
| 5,707,148 A | * | 1/1998 | Visser | C04B 41/009 204/424 |
| 5,902,556 A | * | 5/1999 | Van De Vyver | G01N 25/30 422/174 |
| 6,079,873 A | * | 6/2000 | Cavicchi | G01N 25/4866 374/10 |
| 7,338,640 B2 | * | 3/2008 | Murthy | G01N 25/4893 374/10 |
| 2005/0037499 A1 | | 2/2005 | Ramberg et al. | 436/3 |
| 2007/0212263 A1 | * | 9/2007 | Shin | G01N 27/16 422/95 |
| 2010/0221148 A1 | * | 9/2010 | Oie | G01N 27/16 422/95 |

FOREIGN PATENT DOCUMENTS

| | | | | |
|---|---|---|---|---|
| JP | 2001099798 A | | 4/2001 | ............. G01N 25/32 |
| JP | 2001099801 A | | 4/2001 | ............. G01N 27/16 |
| JP | 2008275588 A | | 11/2008 | ............. G01N 25/30 |
| WO | 2010/022285 A1 | | 2/2010 | ............. G01K 17/00 |
| WO | 2015/028660 A1 | | 3/2015 | ............. G01N 25/32 |

OTHER PUBLICATIONS

International Search Report and Written Opinion, Application No. PCT/EP2014/068495, 17 pages, dated Oct. 10, 2014.

* cited by examiner

SENSOR FOR DETECTING OXIDIZABLE GASES

CROSS-REFERENCE TO RELATED APPLICATIONS

This application is a U.S. National Stage Application of International Application No. PCT/EP2014/068495 filed Sep. 1, 2014, which designates the United States of America, and claims priority to DE Application No. 10 2013 217 465.9 filed Sep. 2, 2013, the contents of which are hereby incorporated by reference in their entirety.

TECHNICAL BACKGROUND

The present disclosure relates to sensors, and more particularly sensors for detecting oxidizable gases.

BACKGROUND

Some known sensors for detecting oxidizable gases operate according to the exothermal principle. These sensors may comprise two sections for detecting temperature, one section of which is coated with a catalytically active material. If a reducing gas, for example $H_2$, $C_3H_6$, is present in the surroundings (assuming there is also oxygen present in the surroundings), the corresponding gas will oxidize on the surface of the catalytically active material. This exothermal reaction raises the temperature of this section (therefore on one side). The gas concentration in the surroundings of the sensor can then be inferred from the measurement of the difference in temperature between the catalytically active surface and the inactive surface.

In the known sensors, the two above-mentioned sections are arranged on a planar surface. This arrangement may be referred to as a hot plate, a plate which is thermally isolated from a base carrier. In order to increase the sensor accuracy, a heating element can be integrated into the sensor element, to operate the sensor at a defined temperature and therefore during defined activity of the catalyst, and also to ensure the possibility of cleaning (thermally burning off impurities/deposits).

These sensors require a large amount of space, since the catalytically active surface and the inactive surface are located on the same side of the sensor element or of the hot plate. This relatively large amount of space required by the sensor is associated with an increased energy demand.

DE 43 17 568 C2 discloses a known sensor, in which the catalytically active surface is located on a heat-transfer body, while the catalytically inactive surface is arranged on another heat-transfer body which is located next to the first heat-transfer body. In each case a thermal element is connected to a heat-transfer body. The thermal elements are in contact with one another via a connection which is arranged in the housing of the sensor. Therefore, this sensor also requires a relatively large amount of space, since the catalytically active surface and the catalytically inactive surface are arranged one next to the other.

U.S. Pat. No. 4,063,898 discloses a sensor which also has a catalytically inactive surface and a catalytically active surface and a device for measuring the thermoelectric voltage between the two surfaces.

A further sensor for detecting oxidizable gases is known from U.S. Pat. No. 4,835,108. Furthermore, a catalytic gas sensor and a method for manufacturing same are described in DE 39 32 880 A1.

SUMMARY OF THE INVENTION

The present disclosure teaches methods for making and/or using, and design of a sensor distinguished by requiring a particularly small amount of space and accordingly having a particularly low energy demand.

In some embodiments of the teachings of the present disclosure, the catalytically active surface and the inactive surface are arranged on different sides of a hot plate and connected to one another through at least one via. The difference in temperature between the two surfaces may be measured directly (that is to say through the cross section of the sensor element) by utilizing the Seebeck effect. The Seebeck effect is based on the formation of an electrical voltage if there is a difference in temperature across a test material. Since this thermoelectric voltage between the catalytically active surface and the inactive surface of the sensor element may be measured in the present case, the sensor element may include at least one via in this region, embodied as a thermal element. The thermoelectric voltage produced between the catalytically active surface and the inactive surface of the sensor element in the region of the at least one via may be measured with a corresponding device. In some embodiments the corresponding device may include a voltage-measuring device. The thermoelectric voltage may serve as a measure of the corresponding difference in temperature, on the basis of which the gas concentration in the surroundings of the sensor can be derived.

The sensor element may comprise a plate thermally isolated from a base carrier, which can be, for example, a corresponding frame. This hot plate is mounted, in some embodiments, on the associated frame by means of four narrow arms. The narrow arms which are used for mounting may ensure low transmission of heat from the hot plate to the surrounding frame.

In some embodiments, the hot plate may have the catalytically active surface on one side, specifically the upper side or underside, and the inactive surface on the opposite side. The two surfaces can be connected to one another through at least one via such as a thermal element.

In some embodiments, the at least one via comprises a material A. The two sides of the via may be in contact via a material B with a comparison point at which there is no temperature gradient present. The material B, or a material with the same thermoelectric properties as the material B, may provide a conductive connector as far as the connection for measuring the voltage. The voltage may be tapped here at the two feed lines made of the material B. The tapped voltage on the two feed lines at a common comparison temperature is therefore proportional to the difference in temperature $\Delta T$ between the two sides of the sensor element or of the hot plate, and is therefore also a measure of the exothermy or gas concentration at the catalytically coated surface.

Therefore, in such embodiments, only two connections to the sensor element (the hot plate) are necessary for measuring the difference in temperature according to the described principle. The sensor therefore may have only two connections to the sensor element.

The measuring effect can be amplified by selectively using materials with a high Seebeck coefficient for the via (material A). In some embodiments, the material A of the at least one via is a material with a high Seebeck coefficient.

The comparison point may be located on the frame of the hot plate. The frame and the arms may be composed of ceramic material. If two identical wires (for example made of copper) or thick film conductor tracks are moved closer to the electronics, only the thermoelectric voltage, which corresponds to the ΔT of the hot plate sides, is measured.

In some embodiments, the sensor comprises a series circuit of thermal pairs over the surface of the sensor element. In this way, the voltage value for the difference in temperature can be increased, with the result that overall an amplified effect is produced if the sensor has a plurality of vias which are connected in series and are made of different materials in the sensor element or in the hot plate. In this context, the vias which are connected in series may be alternately composed of materials A and B, which have Seebeck coefficients which differ from one another. For example, one material (for example material A) can be an n-type conductor, and the other material of the via in the hot plate can be a p-type conductor. However, material B can also be used for this purpose. Generally, the Seebeck coefficients (the thermoelectric power) of the materials A and B differ from one another.

In addition to metals, ceramic conductors or semiconductors are suitable as materials for the via, since ceramic conductors and/or semiconductors usually have a higher thermoelectric power (a larger Seebeck coefficient) and are considered poor thermal conductors. The two sides of the sensor element or of the hot plate may be thus better isolated. The at least one via in the sensor element may include a ceramic conductor.

The at least one via in the sensor element or in the hot plate does not need to be completely filled. In some embodiments, substantially better isolation occurs if only the edges of the via are filled with the conductor. Therefore, in some embodiments only the edge regions of the at least one via in the sensor element are filled with a conductor.

Furthermore, a thick film meander may be "buried" in the sensor element or in the hot plate, to integrate further functionalities such as heating to a defined temperature and/or the measurement of the absolute temperature. Further information can be obtained by means of the defined temperature and the power demand for maintaining it.

The ceramic multi-layer technology (LTCC/HTCC) may be used to construct the sensor element. The low thermal conductivity of such carrier materials promotes the separation of the two temperature levels. Glasses and glass-containing compounds, which are also available as LTCC tapes, are suitable, this is because the thermal conductivity here is even lower than with classic LTCC ceramics. Furthermore, LTCC technology provides the possibility of cost-effective manufacture, freely selectable geometries, multi-layer structures and robustness in harsh ambient conditions.

Various circuitry may be used for evaluating the signals (e.g., a bridge circuit). In such a circuit, given a corresponding placing of the resistors at the comparison point it is also possible at the same time to compensate the absolute temperature fluctuations of the offgas.

The sensor may employ the Seebeck effect with a thermal gas sensor such as a hot plate. Teachings of the present disclosure may provide additional evaluation possibilities, a compact design (use of front side and rear side), and a particularly low power demand. The teachings may eliminate the need for further temperature measuring sensors. In some embodiments, fewer line connections are required. The differential signal can be amplified with a series circuit (thermocolumn), likewise by selecting a "cool" reference measuring point.

A ΔT measurement and absolute T measurement may be carried out by means of the corresponding circuitry.

In some embodiments, the via may be metalized only at the edge, but not adjacently. The catalytically nonactive side may be coupled in a thermally well conducting fashion to the carrier, while this may not be the case with the catalytically active side. The material A and/or B can additionally be covered or contaminated with catalytically active material or can also be located in an intermediate layer.

Use of LTCC/HTCC may provide advantages with respect to its thermal properties and its construction.

BRIEF DESCRIPTION OF THE DRAWINGS

The invention will be explained below in detail with reference to exemplary embodiments and in conjunction with the drawing, in which.

DETAILED DESCRIPTION

Figure 1:
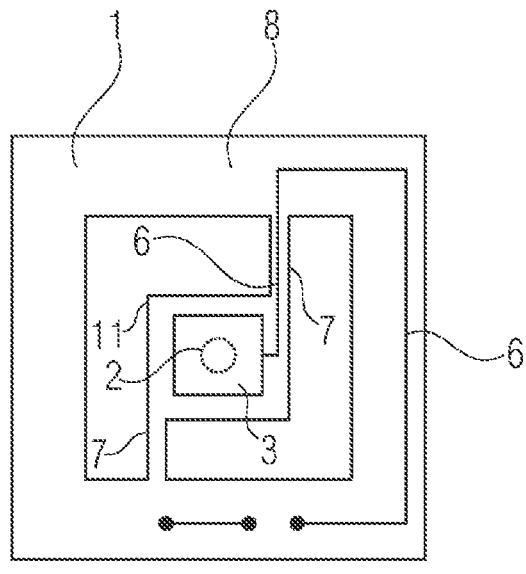
FIG. 1 shows a schematic plan view of a sensor element which is embodied as a hot plate, according to teachings of the present disclosure.
Figure 2:
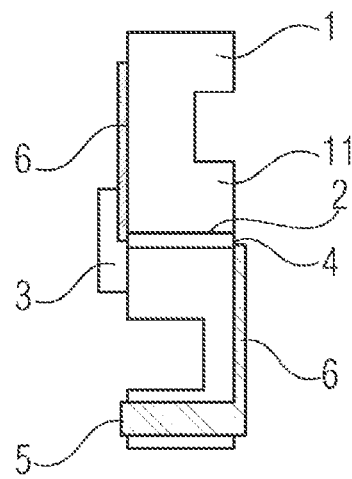
FIG. 2 shows a section through the sensor element in FIG. 1, according to teachings of the present disclosure.

FIGS. 1 and 2 are schematic views of a sensor element 1 which comprises what is referred to as a hot plate 11 which is suspended from a frame 8 by means of two narrow arms 7. On one side of the hot plate 11, here the upper side, there is a catalytically active surface 3, while a catalytically inactive surface 4 is provided on the opposite side. The two surfaces are connected to one another through a via 2, which is embodied as a thermal element.

The sensor element 1 may be part of a sensor designed to detect oxidizable gases taking advantage of the exothermy principle. In particular, the sensor may detect hydrocarbons (HC detection), carbon monoxide (CO detection), or hydrogen ($H_2$ detection). If a reducing gas is present in the surroundings of the sensor element 1, and there is oxygen in the surroundings, the gas on the surface of the catalytically active surface 3 oxidizes. This exothermal reaction raises the temperature on this surface, while the temperature of the catalytically inactive surface 4 does not rise. The difference in temperature between these two surfaces 3 and 4 can be measured directly by means of the cross section of the hot plate 11 by taking advantage of the Seebeck effect. In other words, a thermoelectric voltage is generated at the via 2, embodied as a thermal element, by the corresponding difference in temperature and is measured and evaluated as a measure of the difference in temperature and therefore of the gas concentration in the surroundings of the sensor.

In the embodiment illustrated here, the via 2 is composed of a material A. The two sides of the via 2 are in contact by means of a material B with a comparison point at which a temperature gradient should not be present. In FIGS. 1 and 2, this is illustrated with the lines 6 and the via 5 (comparison point). The corresponding lines 6 which are made of the material B produce the conductive connection as far as the connection for measuring the voltage (not shown). The voltage tap U at the two lines (feed lines) 6 at a common comparison temperature is therefore proportional to the difference in temperature ΔT between the two sides of the hot plate and is therefore also a measure of the exothermy or gas concentration at the catalytically active surface 3.

Figure 3:
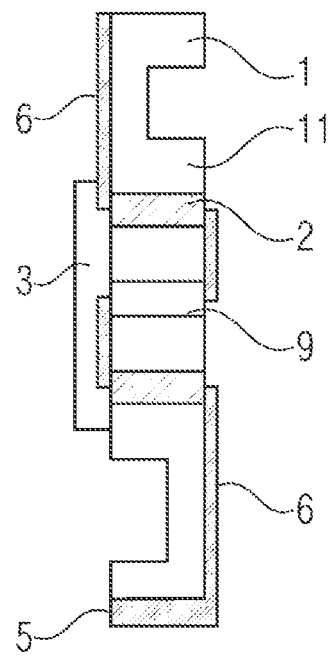
FIG. 3 shows a section through a further embodiment of a sensor element, according to teachings of the present disclosure.

FIG. 3 shows an embodiment of a sensor element 1 which has a series circuit of thermal pairs over the surface of the hot plate. In this context, a plurality of vias 2, 9 are present in the hot plate, wherein the vias 2, 9 are alternately composed of different materials. The Seebeck coefficient (the thermoelectric power) of the material A of the via 2 differs here from the Seebeck coefficients of the vias 9. Moreover, the construction and the measurement principles correspond to those in the embodiments in FIGS. 1 and 2.

Figure 4:
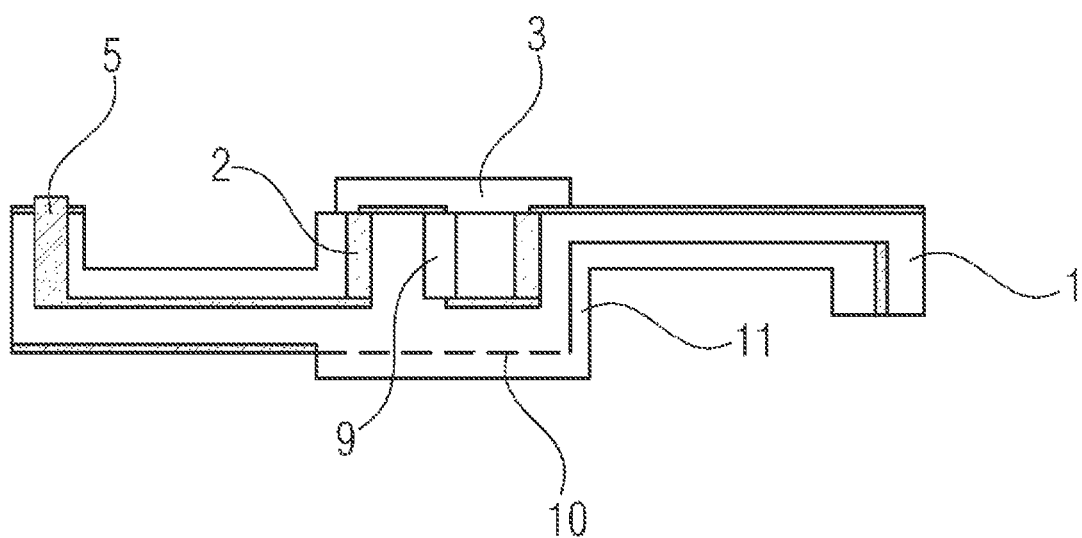
FIG. 4 shows a section through yet a further embodiment of a sensor element, according to teachings of the present disclosure.

FIG. 4 shows an embodiment of a sensor element 1 in which a heater 10 is additionally integrated into the hot plate. This permits the hot plate 11 to be heated to a defined temperature.

What is claimed is:

1. A sensor for detecting oxidizable gases, comprising:
 a catalytically inactive surface and a catalytically active surface forming a sensor element, and
 a device for detecting a difference in temperature between the two surfaces in order to determine a gas concentration in the surroundings of the sensor on the basis of the detected difference in temperature,
 wherein the catalytically active surface is located on a first side and the catalytically inactive surface is located on a second, opposite side of the sensor element, and
 a thermal element running through the sensor element to connect the two surfaces,
 a device for measuring a thermoelectric voltage between the catalytically active surface and the inactive surface as a measure of the difference in temperature and therefore the gas concentration,
 a hot plate mounted on a base carrier by means of narrow arms, on the front side of which hot plate the catalytically active surface is formed, and on the rear side of which the catalytically inactive surface is formed, or vice versa, and
 wherein the thermal element includes at least one via extending through the hot plate and connecting the two surfaces to one another, and in the region of which the thermoelectric voltage is measured.

2. The sensor as claimed in claim 1, wherein the at least one via comprises a material A, in that the two sides of the via are in contact via a material B with a comparison point at which there is no temperature gradient present, and in that the material B produces a conductive connector as far as the connection for measuring the voltage.

3. The sensor as claimed in claim 2, wherein the voltage is tapped at two feed lines made of the material B.

4. The sensor as claimed in claim 2, wherein the material A of the at least one via is a material with a Seebeck coefficient which is high in terms of absolute value.

5. The sensor as claimed in claim 2, wherein the comparison point is located at a frame of the hot plate.

6. The sensor as claimed in claim 1, further comprising only two connections to the sensor element.

7. The sensor as claimed in claim 1, further comprising a series circuit of thermal pairs over the surfaces of the sensor element.

8. The sensor as claimed in claim 7, further comprising a plurality of vias connected in series and made of different materials in the sensor element.

9. The sensor as claimed in claim 8, wherein the vias connected in series are alternately composed of materials A and B, which have Seebeck coefficients which differ from one another.

10. The sensor as claimed in claim 1, wherein the at least one via includes a ceramic conductor.

11. The sensor as claimed in claim 1, wherein only the edge regions of the at least one via are filled with a conductor.

12. A sensor assembly for detecting combustible gases, the assembly comprising:
 a hot plate having a front side and a rear side, the hot plate mounted on a base carrier by means of narrow arms,
 a catalytically active surface disposed on the front side the hot plate,
 a catalytically inactive surface disposed on the rear side of the hot plate,
 a via running through the hot plate and connecting the two surfaces, and
 a device for detecting a difference in temperature between the two surfaces adjacent the via, in order to determine a gas concentration in the surroundings of the sensor on the basis of the detected difference in temperature.

13. The sensor assembly as claimed in claim 12, wherein the voltage is tapped at two feed lines.

14. The sensor assembly as claimed in claim 12, wherein the at least one via comprises a material with a Seebeck coefficient which is high in terms of absolute value.

15. The sensor assembly as claimed in claim 12, further comprising a series circuit of thermal pairs over the surfaces of the hot plate.

16. The sensor assembly as claimed in claim 12, further comprising a plurality of vias connected in series and made of different materials, the plurality of vias running through the hot plate.

17. The sensor assembly as claimed in claim 16, wherein the vias connected in series are alternately composed of materials A and B, which have Seebeck coefficients which differ from one another.

18. The sensor assembly as claimed in claim 12, wherein the at least one via includes a ceramic conductor.

19. The sensor assembly as claimed in claim 12, wherein only the edge regions of the at least one via are filled with a conductor.

* * * * *